United States Patent [19]
Mc Niel

[11] Patent Number: 5,993,404
[45] Date of Patent: Nov. 30, 1999

[54] WALKING BRACE

[76] Inventor: Frank T. Mc Niel, 2023 Inman Way, San Jose, Calif. 95008

[21] Appl. No.: 09/097,960

[22] Filed: Jun. 16, 1998

[51] Int. Cl.$^6$ ..................................................... A61F 5/00
[52] U.S. Cl. .................................................. 602/23; 602/6
[58] Field of Search ................................ 602/1, 5, 6, 10, 602/11, 23, 32, 36, 38; 128/882, 846

[56] References Cited

U.S. PATENT DOCUMENTS

| | | | |
|---|---|---|---|
| 653,179 | 7/1900 | Hughes | 602/23 |
| 2,516,253 | 7/1950 | Pieterick | 602/16 |
| 4,265,230 | 5/1981 | Jordan | 602/23 |
| 5,183,036 | 2/1993 | Spademan | 602/10 |
| 5,236,333 | 8/1993 | Barba, Jr. | 602/5 X |
| 5,342,288 | 8/1994 | Lee et al. | 602/16 X |
| 5,387,184 | 2/1995 | Seitz | 602/23 |

*Primary Examiner*—Richard J. Apley
*Assistant Examiner*—Denise Pothier

[57] ABSTRACT

A leg brace is provided including an upper support for engaging an upper portion of a shin of a user. An intermediate frame includes a plurality of generally vertically oriented rods coupled to the upper support and depending therefrom. Coupled to bottom ends of the rods of the intermediate frame is a lower support for supporting a foot of the user.

2 Claims, 2 Drawing Sheets

WALKING BRACE

BACKGROUND OF THE INVENTION

1. Field of the Invention

The present invention relates to walking devices and more particularly pertains to a new walking brace for allowing a user with a cast to walk without strain.

2. Description of the Prior Art

The use of walking devices is known in the prior art. More specifically, walking devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art walking devices and the like include U.S. Pat. No. 4,058,119; U.S. Pat. No. 5,178,595; U.S. Pat. No. 5,300,016; U.S. Pat. No. 4,910,927; U.S. Pat. No. 5,183,036; and U.S. Pat. Des. 344,589.

In these respects, the walking brace according to the present invention substantially departs from the conventional concepts and designs of the prior art, and in so doing provides an apparatus primarily developed for the purpose of allowing a user with a cast to walk without strain.

SUMMARY OF THE INVENTION

In view of the foregoing disadvantages inherent in the known types of walking devices now present in the prior art, the present invention provides a new walking brace construction wherein the same can be utilized for allowing a user with a cast to walk without strain.

The general purpose of the present invention, which will be described subsequently in greater detail, is to provide a new walking brace apparatus and method which has many of the advantages of the walking devices mentioned heretofore and many novel features that result in a new walking brace which is not anticipated, rendered obvious, suggested, or even implied by any of the prior art walking devices, either alone or in any combination thereof.

To attain this, the present invention generally comprises an upper support having a pad with a U-shaped configuration. The pad is thus defined by a pair of generally linear extents and an arcuate extent situated therebetween. As shown in FIG. 4, the pad has a constant square cross-section. Also, a first terminal end of the pad is elevated with respect to a second terminal end thereof. The upper support further includes four hollow sleeves having top ends mounted to a bottom surface of the pad adjacent to ends of the generally linear extents. The sleeves extend downwardly from the pad in parallel relationship. The sleeves that are situated adjacent to the arcuate extent of the pad are spaced closer that those positioned adjacent to the terminal ends of the pad. An intermediate frame is provided comprising four vertically oriented rods with upper halves which remain in parallel relationship. Such upper halves of the rods further have a plurality of linearly aligned, diametrically opposed apertures formed therein. These apertures are adapted for coupling with the sleeves of the upper support at selected lengths via bolts and wing nuts. Note FIG. 3. The vertically oriented rods of the intermediate frame include a pair of front rods and a pair of rear rods. The upper halves of the front rods have bottom ends coupled via a front horizontal bar situated beneath the arcuate extent of the pad of the upper support. Further, the rear rods have bottom ends thereof coupled to the bottom ends of the front rods via a pair of side horizontal bars. Each of the vertically oriented rods also include lower halves. The lower halves of the front rods remain in general alignment with the upper halves thereof. In contrast, the lower halves of the rear rods bow rearwardly and outwardly, as shown in FIGS. 1 & 3. Next provided is a lower support including a generally planar rectangular bottom plate. Tile bottom plate is coupled between bottom ends of the lower halves of the vertically oriented rods of the intermediate frame. As shown in FIGS. 1 & 2, a pair of arcuate tracks each have a width equal to less than ¼ that of the bottom plate. The tracks further have ends coupled beneath front and rear edges of the bottom plate. An apex of each track is situated approximately 3 inches from the rear edge of the bottom plate. Finally, two pairs of straps are provided including an upper pair of straps each having an inboard end coupled to one of the terminal ends of the pad. Associated therewith is a lower pair of straps each having an inboard end coupled to the bottom end of the upper half of one of the rear rods of the intermediate frame. It should be noted that each of the straps has an outboard end with a pile fastener mounted thereon. By this structure, the straps may be interconnected to engage a rear of a leg of a user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new walking brace apparatus and method which has many of the advantages of the walking devices mentioned heretofore and many novel features that result in a new walking brace which is not anticipated, rendered obvious, suggested, or even implied by any of the prior art walking devices, either alone or in any combination thereof.

It is another object of the present invention to provide a new walking brace which may be easily and efficiently manufactured and marketed.

It is a further object of the present invention to provide a new walking brace which is of a durable and reliable construction.

An even further object of the present invention is to provide a new walking brace which is susceptible of a low cost of manufacture with regard to both materials and labor, and which accordingly is then susceptible of low prices of sale to the consuming public, thereby making such walking brace economically available to the buying public.

Still yet another object of the present invention is to provide a new walking brace which provides in the apparatuses and methods of the prior art some of the advantages thereof, while simultaneously overcoming some of the disadvantages normally associated therewith.

Still another object of the present invention is to provide a new walking brace for allowing a user with a cast to walk without strain.

Even still another object of the present invention is to provide a new walking brace that includes an upper support for engaging an upper portion of a shin of a user. An intermediate frame includes a plurality of generally vertically oriented rods coupled to the upper support and depending therefrom. Coupled to bottom ends of the rods of the intermediate frame is a lower support for supporting a foot of the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
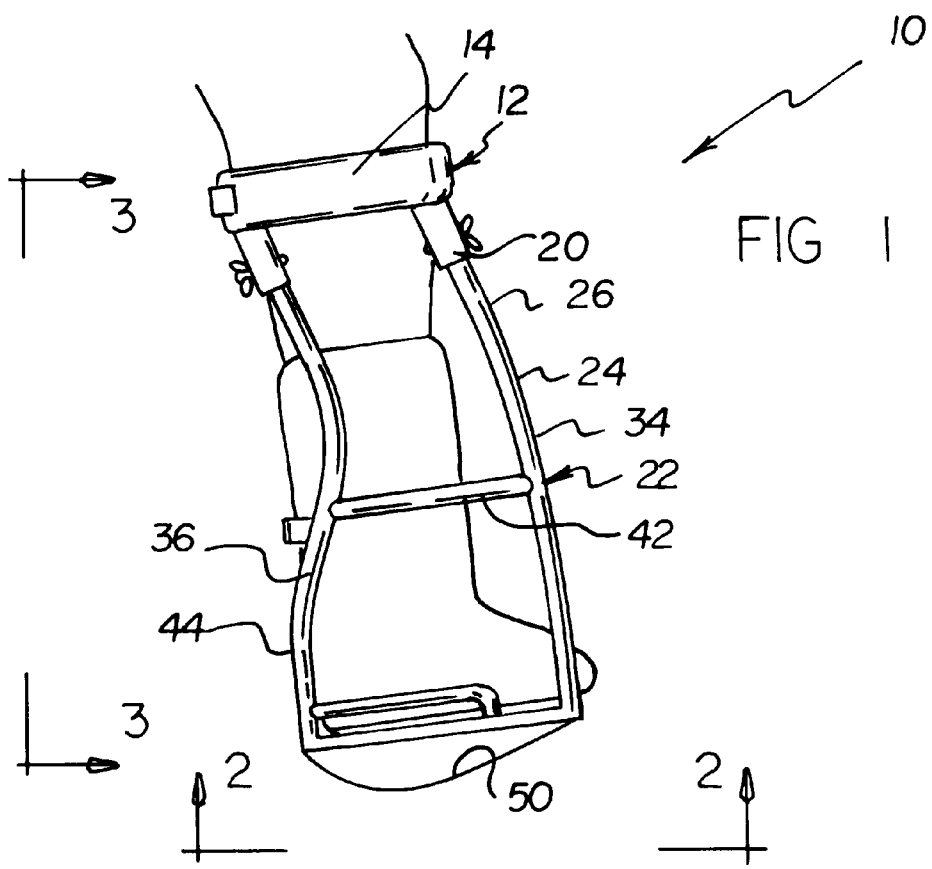
FIG. 1 is a side view of a new walking brace according to the present invention.

With reference now to the drawings, and in particular to FIGS. 1 through 4 thereof, a new walking brace embodying the principles and concepts of the present invention and generally designated by the reference numeral 10 will be described.

Figure 4:
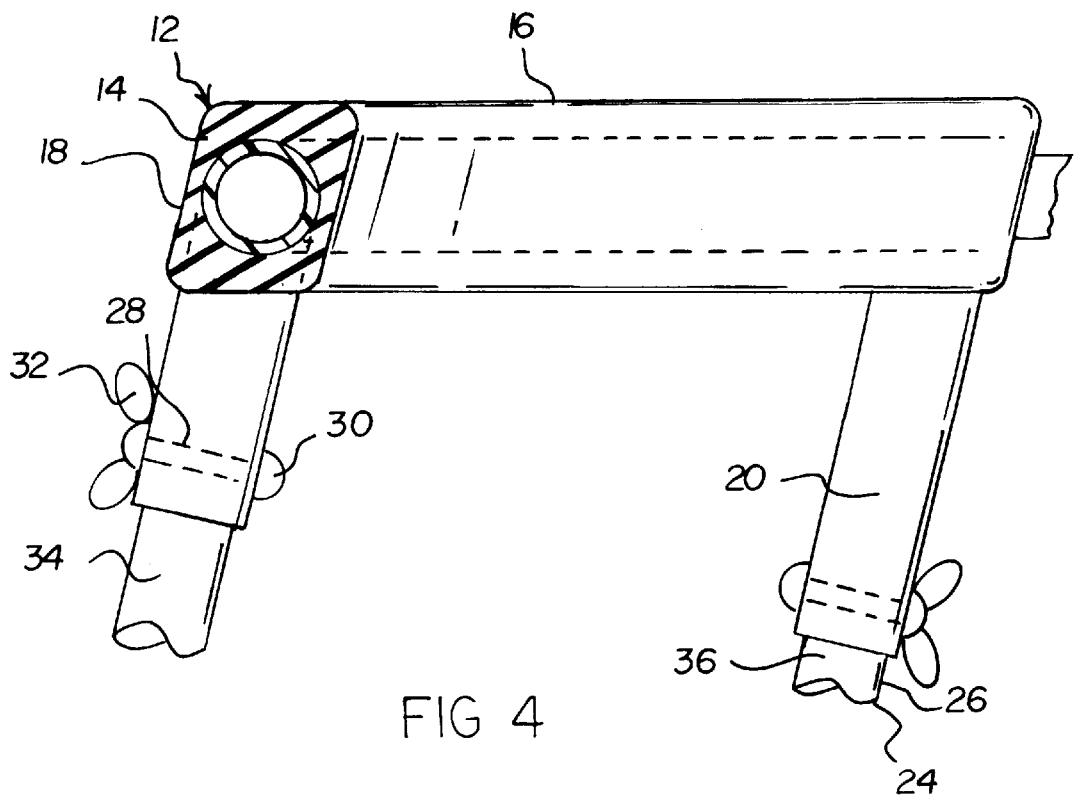
FIG. 4 is a side cross-sectional view of the present invention.

The present invention, designated as numeral 10, includes an upper support 12 having a pad 14 with a U-shaped configuration. The pad is thus defined by a pair of generally linear extents 16 and an arcuate extent 18 situated therebetween. As shown in FIG. 4, the pad has a constant square cross-section. Also, a first terminal end of the pad may be elevated with respect to a second terminal end thereof. As such, the pad resides in an angled plane during use. It is imperative that the second terminal end correspond with an inner side of a leg, as will become apparent.

The upper support further includes four hollow sleeves 20 having top ends mounted to a bottom surface of the pad adjacent to ends of the generally linear extents. The sleeves extend downwardly from the pad in parallel relationship. The sleeves that are situated adjacent to the arcuate extent of the pad are spaced closer that those positioned adjacent to the terminal ends of the pad.

An intermediate frame 22 is provided comprising four vertically oriented rods 24 with upper halves 26 which remain in parallel relationship. Such upper halves of the rods further have a plurality of linearly aligned, diametrically opposed apertures 28 formed therein. These apertures are adapted for coupling with the sleeves of the upper support at selected lengths via bolts 30 and wing nuts 32. Note FIG. 3.

Figure 3:
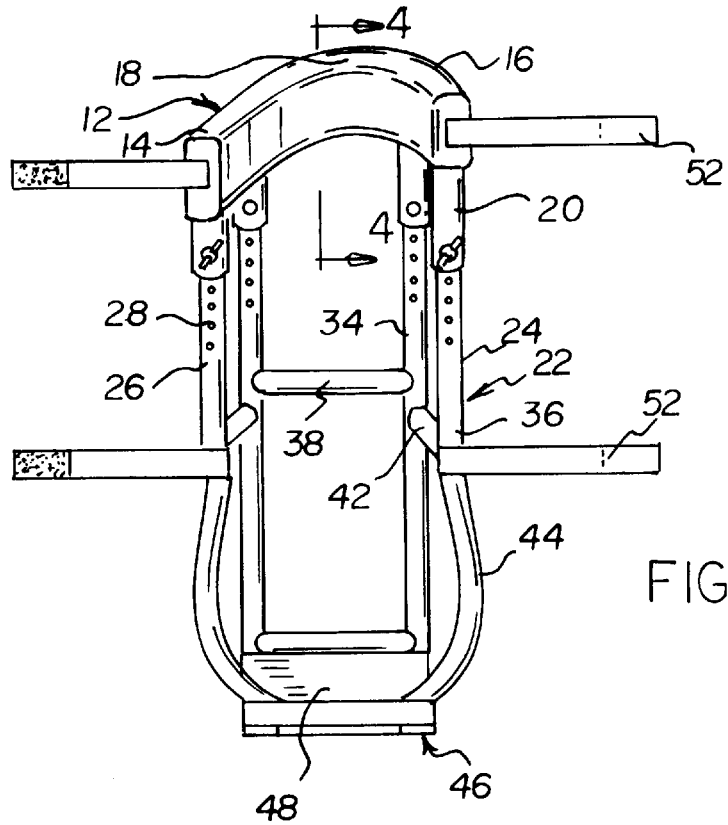
FIG. 3 is a rear view of the present invention.

The vertically oriented rods of the intermediate frame include a pair of front rods 34 and a pair of rear rods 36. The upper halves of the front rods have bottom ends coupled via a front horizontal bar 38 situated beneath the arcuate extent of the pad of the upper support. Further, the rear rods have bottom ends thereof coupled to the bottom ends of the front rods via a pair of side horizontal bars 42. Each of the vertically oriented rods also include lower halves 44. The lower halves of the front rods remain in general alignment with the upper halves thereof. In contrast, the lower halves of the rear rods bow rearwardly and outwardly, as shown in FIGS. 1 & 3. Also shown in such Figures are additional horizontal bars mounted on the rods of the intermediate frame at lower ends thereof.

Figure 2:
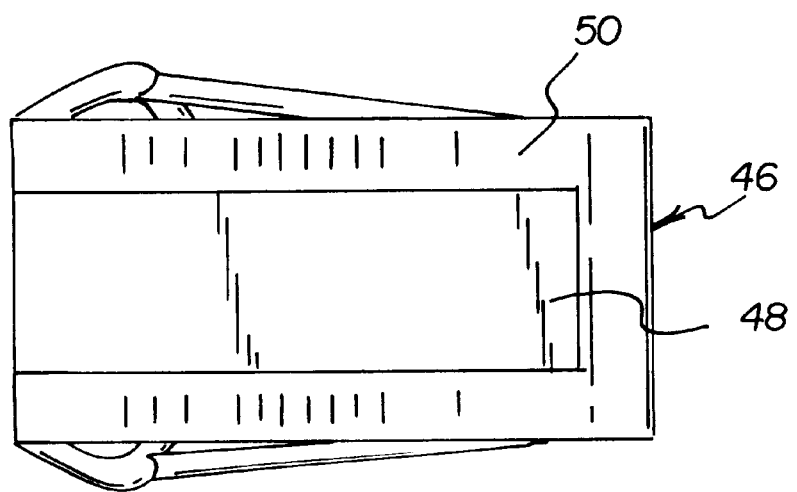
FIG. 2 is a bottom view of the present invention.

The leg brace also includes a lower support 46 including a generally planar rectangular bottom plate 48. The bottom plate is coupled between bottom ends of the lower halves of the vertically oriented rods of the intermediate frame. As shown in FIGS. 1 & 2, a pair of arcuate tracks 50 are provided each having a width equal to less than ¼ that of the bottom plate. The tracks further have ends coupled beneath front and rear edges of the bottom plate. An apex of each track is situated approximately 3 inches from the rear edge of the bottom plate. As an option, the tracks may be lined with a non-slip cover or tread.

Finally, two pairs of straps 52 are provided including an upper pair of straps each having an inboard end coupled to one of the terminal ends of the pad. Associated therewith is a lower pair of straps each having an inboard end coupled to the bottom end of the upper half of one of the rear rods of the intermediate frame. It should be noted that each of the straps has an outboard end with a pile fastener mounted thereon. By this structure, the straps may be interconnected to engage a rear of a leg of a user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A leg brace for an injured leg with a cast comprising, in combination:

an upper support including a pad with a U-shaped configuration defined by a pair of generally linear extents and an arcuate extent situated therebetween, the pad having a constant rectangular cross-section and first and second terminal ends, the upper support further including four hollow sleeves having top ends mounted to a bottom surface of the pad adjacent to ends of the generally linear extents and extending downwardly therefrom in parallel relationship, wherein the sleeves that are situated adjacent to the arcuate extent of the pad are spaced closer than those positioned adjacent to the terminal ends of the pad;

an intermediate frame comprising four vertically oriented rods with upper halves which remain in parallel relationship and have a plurality of linearly aligned, diametrically opposed apertures formed therein for coupling with the sleeves of the upper support at selected lengths with bolts and wing nuts, the vertically oriented rods including a pair of front rods and a pair of rear rods, the upper halves of the front rods having bottom ends thereof coupled with a front horizontal bar situated beneath the arcuate extent of the pad of the upper support and the rear rods having bottom ends thereof coupled to the bottom ends of the front rods with a pair of side horizontal bars, each of the vertically oriented rods further including lower halves, the lower halves of the front rods remaining in general alignment with the upper halves thereof and the lower halves of the rear rods bowing rearwardly and outwardly;

a lower support including a generally planar rectangular bottom plate coupled between bottom ends of the lower halves of the vertically oriented rods of the intermediate frame and a pair of arcuate tracks each having a width equal to less than ¼ that of the bottom plate and having ends coupled beneath front and rear edges of the bottom plate, wherein an apex of each track is situated approximately 3 inches from the rear edge of the bottom plate; and two pairs of straps including an upper pair of straps and a lower pair of straps, the upper pair of straps each having an inboard end coupled to one of the terminal ends of the pad and having an outboard end with a pile fastener mounted thereon, the lower pair of straps each having an inboard end coupled to the bottom end of the upper half of one of the rear rods of the intermediate frame and an outboard end with a pile fastener mounted thereon.

2. A leg brace for a leg with a cast thereon, the leg brace comprising:

an upper support including a pad with a U-shaped configuration defined by a pair of generally linear extents and an arcuate extent situated therebetween, the pad having first and second terminal ends;

the upper support further including four sleeves having top ends mounted to a bottom surface of the pad adjacent to ends of the generally linear extents and extending downwardly therefrom in parallel relationship;

an intermediate frame comprising four vertically oriented rods with upper halves which remain in parallel relationship and have a plurality of linearly aligned, diametrically opposed apertures formed therein and coupled to the sleeves of the upper support at selected lengths;

the vertically oriented rods including a pair of front rods and a pair of rear rods;

the upper halves of the front rods having bottom ends thereof coupled with a front horizontal bar situated beneath the arcuate extent of the pad of the upper support;

the rear rods having bottom ends thereof coupled to the bottom ends of the front rods with a pair of side horizontal bars, each of the vertically oriented rods further including lower halves, the lower halves of the front rods remaining in general alignment with the upper halves thereof and the lower halves of the rear rods bowing rearwardly and outwardly;

a lower support including a bottom plate coupled between bottom ends of the lower halves of the vertically oriented rods of the intermediate frame and a pair of arcuate tracks having ends coupled beneath front and rear edges of the bottom plate; and two pairs of straps including an upper pair of straps and a lower pair of straps, the upper pair of straps each having an inboard end coupled to one of the terminal ends of the pad and having an outboard end with a pile fastener mounted thereon, the lower pair of straps each having an inboard end coupled to the bottom end of the upper half of one of the rear rods of the intermediate frame and an outboard end with a pile fastener mounted thereon.

\* \* \* \* \*